(12) United States Patent
Lee

(10) Patent No.: US 8,774,894 B2
(45) Date of Patent: *Jul. 8, 2014

(54) ELECTROENCEPHALOGRAM (EEG) CLUSTER ELECTRODES

(75) Inventor: Michael Lee, Carmel, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/053,043

(22) Filed: Mar. 21, 2011

(65) Prior Publication Data

US 2011/0257502 A1    Oct. 20, 2011

Related U.S. Application Data

(60) Provisional application No. 61/315,924, filed on Mar. 20, 2010, provisional application No. 61/315,925, filed on Mar. 20, 2010, provisional application No. 61/315,929, filed on Mar. 20, 2010.

(51) Int. Cl.
*A61B 5/0478* (2006.01)
*A61B 5/0476* (2006.01)
*A61B 5/0408* (2006.01)

(52) U.S. Cl.
CPC .................................. *A61B 5/04085* (2013.01)
USPC ............................ 600/383; 600/544; 600/393

(58) Field of Classification Search
USPC .......... 600/372, 382, 383, 390, 393, 544–545
See application file for complete search history.

(56) References Cited

U.S. PATENT DOCUMENTS

| 3,882,846 | A | * | 5/1975 | Fletcher et al. | 600/395 |
|---|---|---|---|---|---|
| 4,170,225 | A | * | 10/1979 | Criglar et al. | 600/546 |
| 4,202,354 | A | * | 5/1980 | Smith et al. | 600/544 |
| 5,038,782 | A | * | 8/1991 | Gevins et al. | 600/383 |
| 5,772,591 | A | * | 6/1998 | Cram | 600/383 |
| 5,938,597 | A | * | 8/1999 | Stratbucker | 600/382 |
| 6,477,407 | B1 | | 11/2002 | Klistorner et al. | |
| 6,510,333 | B1 | * | 1/2003 | Licata et al. | 600/383 |
| 6,807,438 | B1 | * | 10/2004 | Brun Del Re et al. | 600/372 |
| 2006/0058694 | A1 | * | 3/2006 | Clark et al. | 600/509 |
| 2006/0089557 | A1 | * | 4/2006 | Grajales et al. | 600/508 |
| 2006/0173364 | A1 | * | 8/2006 | Clancy et al. | 600/485 |
| 2006/0293578 | A1 | * | 12/2006 | Rennaker, II | 600/378 |

(Continued)

FOREIGN PATENT DOCUMENTS

DE    69937234    3/2008

OTHER PUBLICATIONS

Office Action, issued by the United States Patent and Trademark Office in connection with U.S. Appl. No. 13/053,016, on Aug. 5, 2013, 16 pages.

(Continued)

*Primary Examiner* — Lee S Cohen
*Assistant Examiner* — Erin M Cardinal
(74) *Attorney, Agent, or Firm* — Hanley, Flight & Zimmerman, LLC

(57) ABSTRACT

Embodiments described herein include devices and systems comprising sensor electrodes. Each sensor electrode comprises contacts positioned adjacent one another to form a pattern. Signal outputs are coupled to the contacts. A signal output is connected to each contact. One or more processors are coupled to the signal outputs. The processor separately processes each of the signal outputs.

48 Claims, 10 Drawing Sheets

(56) References Cited

U.S. PATENT DOCUMENTS

| | | | |
|---|---|---|---|
| 2007/0055169 A1 | 3/2007 | Lee et al. | |
| 2007/0225585 A1* | 9/2007 | Washbon et al. | 600/393 |
| 2008/0091089 A1 | 4/2008 | Guillory et al. | |
| 2008/0146894 A1 | 6/2008 | Bulkes et al. | |
| 2009/0253996 A1 | 10/2009 | Lee et al. | |
| 2010/0010364 A1* | 1/2010 | Verbitskiy | 600/544 |
| 2010/0145216 A1* | 6/2010 | He et al. | 600/544 |
| 2010/0274153 A1* | 10/2010 | Tucker et al. | 600/544 |
| 2011/0257937 A1* | 10/2011 | Lee | 702/189 |
| 2012/0065536 A1* | 3/2012 | Causevic et al. | 600/544 |
| 2012/0226127 A1* | 9/2012 | Asjes et al. | 600/383 |
| 2012/0245439 A1* | 9/2012 | Andre et al. | 600/310 |

OTHER PUBLICATIONS

Notice of Allowance and Fee(s) Due, issued by the United States Patent and Trademark Office in connection with U.S. Appl. No. 13/053,016, on Dec. 13, 2013, 9 pages.

Examination Report, with English Language Version, issued by the German Patent & Trademark Office in connection with German Patent Application No. 112011100979.8 on Dec. 17, 2013, 24 pages.

International Search Report, issued by the International Searching Authority in connection with corresponding International patent application No. PCT/US2011/29262, mailed on Jul. 22, 2011, 2 pages.

Written Opinion, issued by the International Searching Authority in connection with corresponding International patent application No. PCT/US2011/29262, mailed on Jul. 22, 2011, 7 pages.

International Preliminary Report on Patentability and Written Opinion, issued by the International Searching Authority in connection with corresponding International patent application No. PCT/US2011/29262, mailed on Jul. 22, 2011, 8 pages.

\* cited by examiner

.33* A +.67 * B = C

.33* A * T0 +.67 * B * delay T1 = Virtual sensor

Digital processing

Model of transient response of a static impulse S1(t)

Model of transient response of as step function S2(t)

Function to calculate optimum coefficients

Actual Voltage as function of time V(t)

$V(t) - k1(t)*S1(t) - k2(t)*S2(t) = Output(t)$

ELECTROENCEPHALOGRAM (EEG) CLUSTER ELECTRODES

RELATED APPLICATIONS

This application claims the benefit of U.S. Patent Application No. 61/315,924, filed Mar. 20, 2010.

This application claims the benefit of U.S. Patent Application No. 61/315,925, filed Mar. 20, 2010.

This application claims the benefit of U.S. Patent Application No. 61/315,929, filed Mar. 20, 2010.

This application is related to the following U.S. patent application Ser. No. 11/804,517, filed May 17, 2007; Ser. No. 11/804,555, filed May 17, 2007; Ser. No. 11/779,814, filed Jul. 18, 2007; Ser. No. 11/500,678, filed Aug. 8, 2006; Ser. No. 11/845,993, filed Aug. 28, 2007; Ser. No. 11/835,634, filed Aug. 8, 2007; Ser. No. 11/846,068, filed Aug. 28, 2007; Ser. No. 12/180,510, filed Jul. 25, 2008; Ser. No. 12/206,676, filed Sep. 8, 2008; Ser. No. 12/206,700, filed Sep. 8, 2008; Ser. No. 12/206,702, filed Sep. 8, 2008; Ser. No. 12/244,737, filed Oct. 2, 2008; Ser. No. 12/244,748, filed Oct. 2, 2008; Ser. No. 12/263,331, filed Oct. 31, 2008; Ser. No. 12/244,751, filed Oct. 2, 2008; Ser. No. 12/244,752, filed Oct. 2, 2008; Ser. No. 12/263,350, filed Oct. 31, 2008; Ser. No. 11/430,555, filed May 9, 2006; Ser. No. 11/681,265, filed Mar. 2, 2007; Ser. No. 11/852,189, filed Sep. 7, 2007; Ser. No. 11/959,399, filed Dec. 18, 2007; Ser. No. 12/326,016, filed Dec. 1, 2008; 61/225,186, filed Jul. 13, 2009.

TECHNICAL FIELD

The embodiments herein relate to electrodes and, more particularly, to electrodes for sensing electrical activity in tissue.

BACKGROUND

Traditionally EEG electrodes are placed equidistant from each other and cover all of the area of the head. This provides a map or image of the brain wave energy over the surface area of the brain. More advanced EEGs (e.g., available from EmSense Corporation, San Francisco, Calif.) that are targeted at specific measurements are designed with a single electrode at a specific position to produce a specific state or response. The limitation of this methodology is that there is some variation in brain position and structure and the optimum position for the measurement cannot be determined for each individual without extensive experimentation.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIGS. 7A and 7B show a method for processing signals from a plurality of independent contacts 102-110 of an electrode in order to select high quality contact(s) and/or reject low quality contact(s) in an electrode based on signals collected by the electrodes, under an embodiment.

DETAILED DESCRIPTION

Systems and methods for cluster electrodes and signal processing are described herein. The systems and methods described herein include a multiplicity of contacts for each sensor. This solution allows for the optimum measurement location of the specific state or response. Thus, in contrast to the contact grid known in the art, the embodiments described herein measure signals at locations targeted to optimize recording of a specific state or response.

Figure 1:
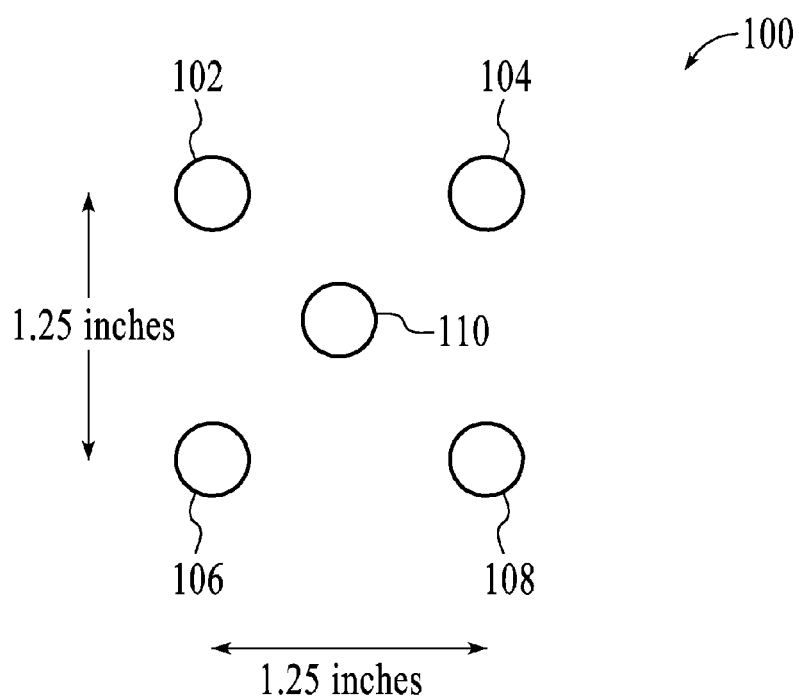
FIG. 1 is a sensor or electrode comprising a plurality of contacts, under an embodiment.

FIG. 1 is a sensor or electrode 100 comprising a plurality of contacts 102-110, under an embodiment. The electrode of an embodiment includes five (5) contacts 102-110, but is not limited to this number of contacts. The contacts 102-110 of the electrode are in close proximity to one another and, in this example embodiment, the contacts 102-110 are located within an area of approximately 1.25 inches by 1.25 inches. The five contacts 102-110 are also shown in an arrangement that has each of four contacts 102-108 positioned in each of the corners of a rectangular configuration, while one contact 110 is positioned in a central region of the rectangular configuration.

In contrast to conventional sensor electrodes for measuring biometric signals, which use silver/silver chloride contacts, the electrodes 100 of an embodiment include gold contacts 102-110 comprising a smooth surface. Therefore, the contacts 102-110 described herein enable measurement of signals (e.g., EEG) through the hair. These contacts effectively cover the skin completely forcing the sweat glands to open up and provide a conductive path between the inner layers of the skin and the circulatory system and the gold contact. Thus, the contacts of an embodiment are non-invasive, through-the-hair contacts, and are used without gels. The electrode formed from numerous contacts allows a configuration in which each electrode provides maximum spatial resolution in a targeted region. Furthermore, this configuration takes into account individual anatomical brain differences.

Figure 2:
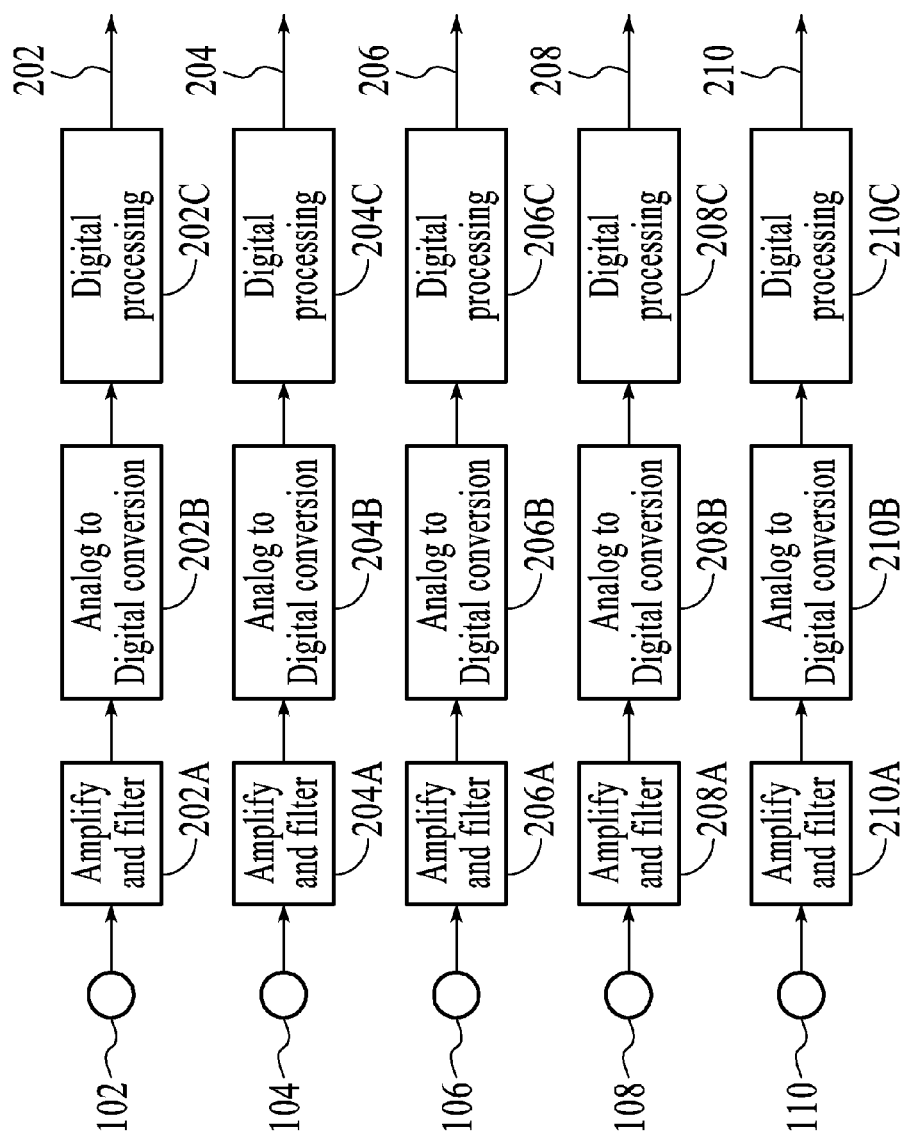
FIG. 2 is a block diagram showing independent contact processing for five (5) contacts of an electrode, under an embodiment.

The signals collected by each contact 102-110 of the electrode of an embodiment are independently processed in a separate signal processing path 202-210. FIG. 2 is a block diagram showing independent contact signal processing 202-210 for five (5) contacts 102-110 of an electrode, under an embodiment. The processing of an embodiment includes signal processing appropriate to a type of signal received or collected by a contact corresponding to the signal processing path. As an example, the processing path of an embodiment includes amplifying and filtering 202A-210A, signal conversion 202B-210B (e.g., analog to digital conversion), and digital processing 202C-210C, to name a few.

Figure 3:
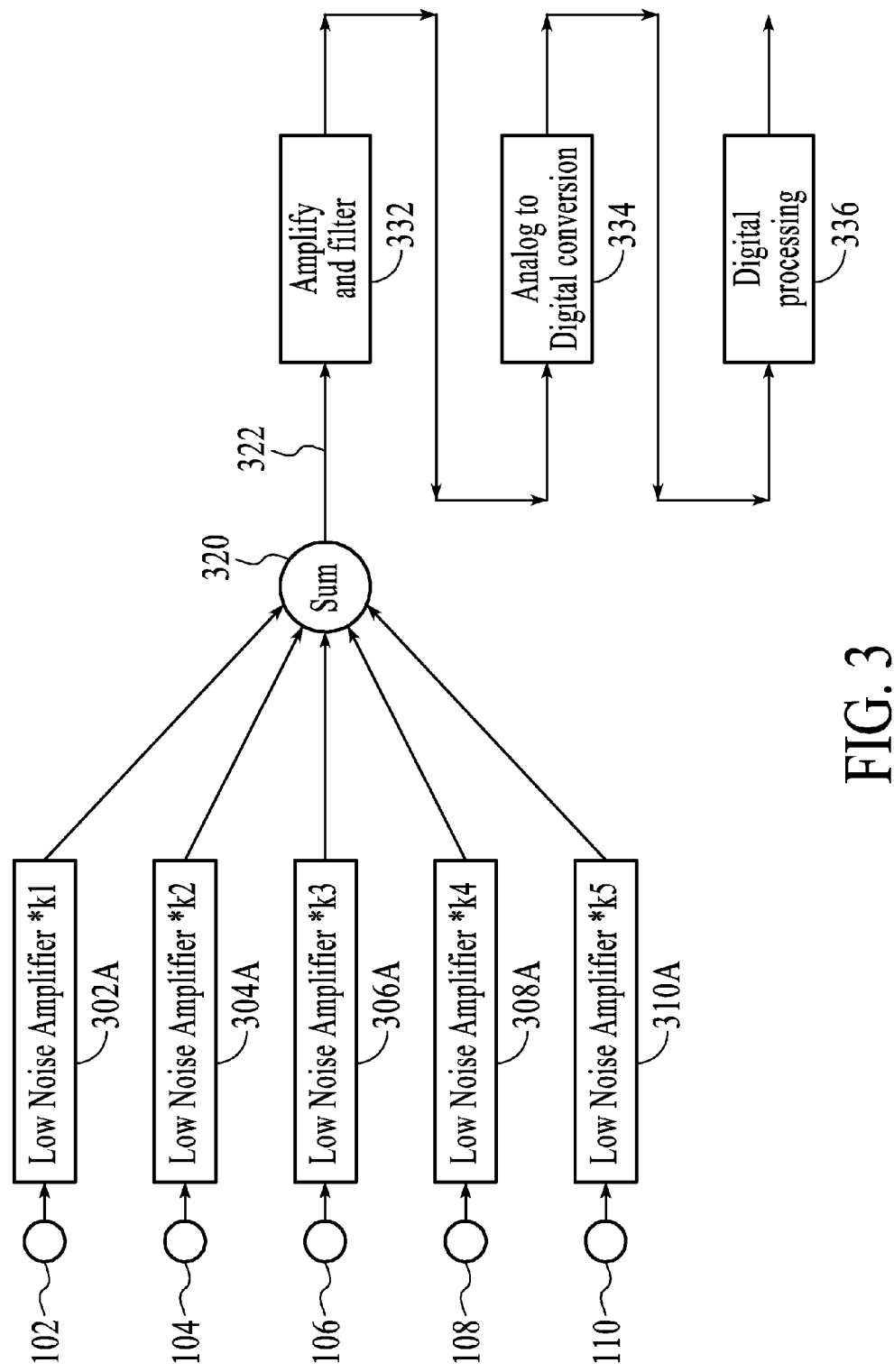
FIG. 3 is a block diagram for processing and combining signals from a plurality of independent contacts of an electrode to provide a virtual sensor, under an embodiment.
Figure 4:
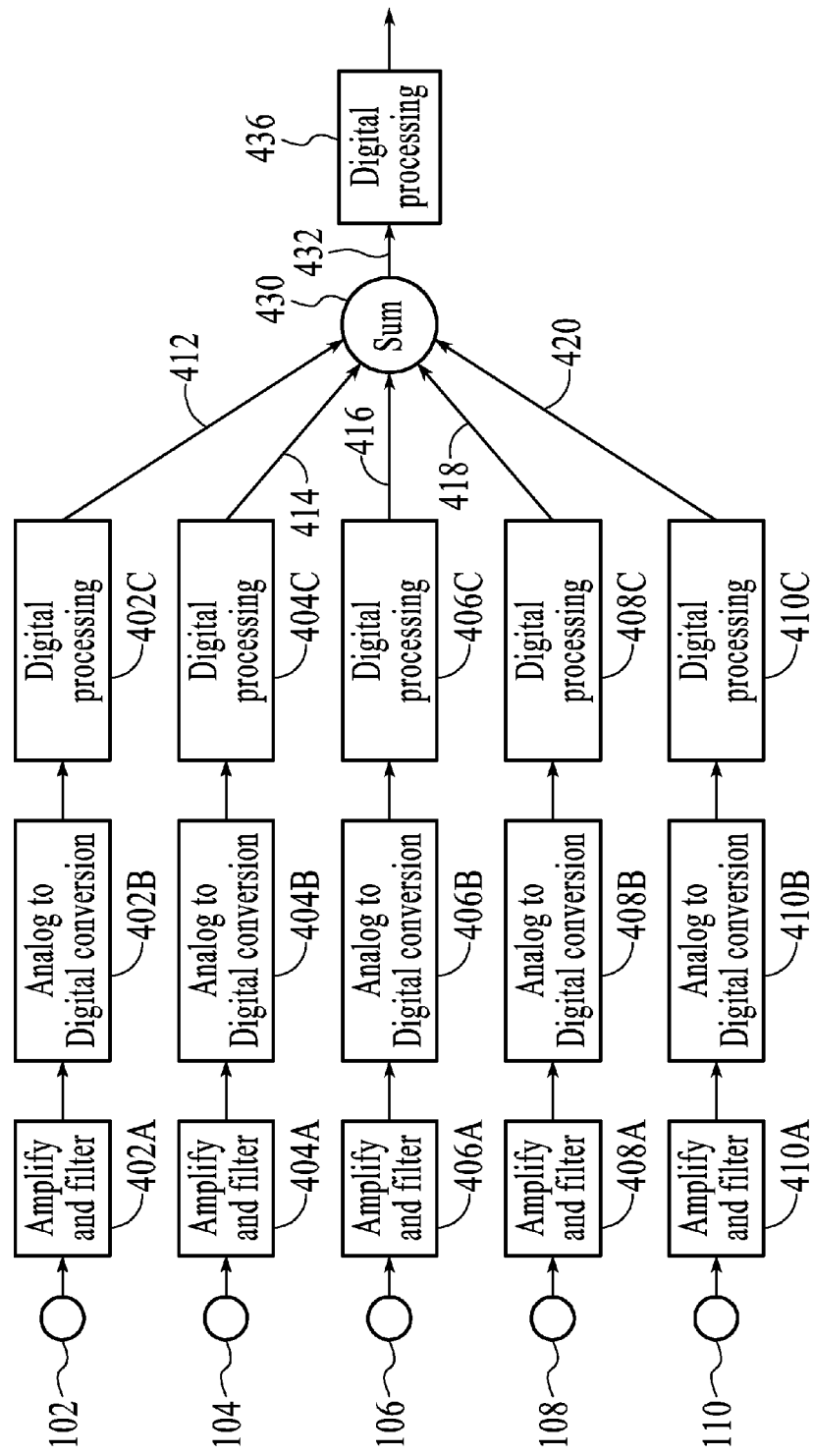
FIG. 4 is a block diagram for processing and combining signals from a plurality of independent contacts of an electrode to provide a virtual sensor, under an alternative embodiment.
Figure 5:
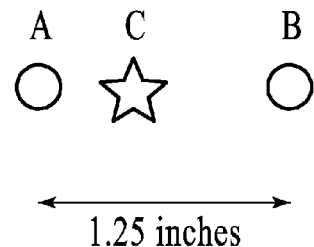
FIG. 5 shows a method for processing and combining signals from multiple independent contacts of an electrode in a weighted and phased manner to provide a virtual contact signal, under an embodiment.

The signals collected by each contact of the electrode of an embodiment are combined in a weighted manner to provide a virtual sensor that could be at any position within the array of contacts. FIGS. 3-5 are block diagrams showing different methods for processing and combining signals from a plurality of independent contacts of an electrode to provide a virtual sensor, under an embodiment.

FIG. 3 is a block diagram for processing and combining signals from a plurality of independent contacts of an electrode to provide a virtual sensor, under an embodiment. In this embodiment, a weighting factor is applied to the output of each contact. For example, a weighting factor of k1 is applied 302A to an output of a first contact 102, a weighting factor of k2 is applied 304A to an output of a second contact 104, a weighting factor of k3 is applied 306A to an output of a third contact 106, a weighting factor of k4 is applied 308A to an output of a fourth contact 108, and a weighting factor of k5 is applied 310A to an output of a fifth contact 110. The weighting factor applied to each signal can be of any type and/or weight appropriate to the type of signal received or collected by the contact corresponding to the signal processing path. Following application of the weighting factor to each contact output, the signals from all contacts 102-110 forming the electrode are summed 320 to form a single signal 322, and further processing is applied to the signal output of the summing operation (e.g., amplifying and/or filtering 332, signal conversion 334 (e.g., analog to digital conversion), digital processing 336, etc.).

FIG. 4 is a block diagram for processing and combining signals from a plurality of independent contacts 102-110 of an electrode to provide a virtual sensor, under an alternative embodiment. In this embodiment, a signal of each contact 102-110 of the electrode is processed independently in a separate signal processing path 402-410. The independently processed signals from each of the contacts 102-110 are then summed to form a single signal, and further processing is applied to the signal output of the summing operation (e.g., amplifying, filtering, signal conversion (e.g., analog to digital conversion), digital processing, etc.).

For example, amplifying and filtering 402A, analog to digital conversion 402B, and digital processing 402C are applied to an output of a first contact 102 to form a first processed signal 412, amplifying and filtering 404A, analog to digital conversion 404B, and digital processing 404C are applied to an output of a second contact 104 to form a second processed signal 414, amplifying and filtering 406A, analog to digital conversion 406B, and digital processing 406C are applied to an output of a third contact 106 to form a third processed signal 416, amplifying and filtering 408A, analog to digital conversion 408B, and digital processing 408C are applied to an output of a fourth contact 108 to form a fourth processed signal 418, and amplifying and filtering 410A, analog to digital conversion 410B, and digital processing 410C are applied to an output of a fifth contact 110 to form a fifth processed signal 420. Following creation of the five processed signals 412-420, the five processed signals 412-420 are summed 430 to form a single signal 432, and further processing 436 is applied to the signal output 432 of the summing operation 430 (e.g., amplifying, filtering, signal conversion (e.g., analog to digital conversion), digital processing, etc.).

FIG. 5 shows a method for processing and combining signals from multiple independent contacts of an electrode in a weighted and phased manner to provide a virtual contact signal, under an embodiment. While this example shows a combining operation for signals of two contacts A and B, the embodiment is not so limited. For example, a weighting factor (e.g., 0.33) is applied to a signal output of a first contact A, and a weighting factor (e.g., 0.67) is applied to a signal output of a second contact B. The weighting factor applied to each signal can be of any type and/or weight appropriate to the type of signal received or collected by the contact corresponding to the signal processing path. Following application of the weighting factor to the signal outputs of each of the two contacts A and B, the weighted signals from the contacts A and B are summed to form a single virtual contact signal representing a virtual contact C. While not shown, further processing (e.g., amplifying, filtering, signal conversion (e.g., analog to digital conversion), digital processing, etc.) can be applied to the virtual contact signal output.

Figure 6:
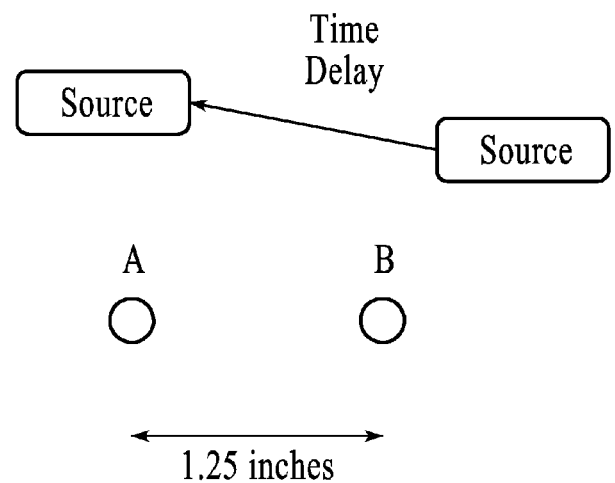
FIG. 6 shows a method for processing and combining signals from multiple independent contacts of an electrode in a weighted and phased manner to provide a virtual contact signal, under an alternative embodiment.

FIG. 6 shows a method for processing and combining signals from multiple independent contacts of an electrode in a weighted and phased manner to provide a virtual contact signal, under an alternative embodiment. While this example shows a combining operation for signals of two contacts, the embodiment is not so limited. For example, a weighting factor (e.g., 0.33) and a time factor (e.g. T0) is applied to a signal output of a first contact A, and a weighting factor (e.g., 0.67) and a time factor (e.g. T1) is applied to a signal output of a second contact B. The weighting factor and/or time factor applied to each signal can be of any type and/or weight appropriate to the type of signal received or collected by the contact corresponding to the signal processing path. Following application of the weighting factor to the signal outputs of each of the two contacts A and B, the weighted signals from the contacts A and B are summed to form a single virtual contact signal. While not shown, further processing (e.g., amplifying, filtering, signal conversion (e.g., analog to digital conversion), digital processing, etc.) can be applied to the virtual contact signal output.

Figure 7A:
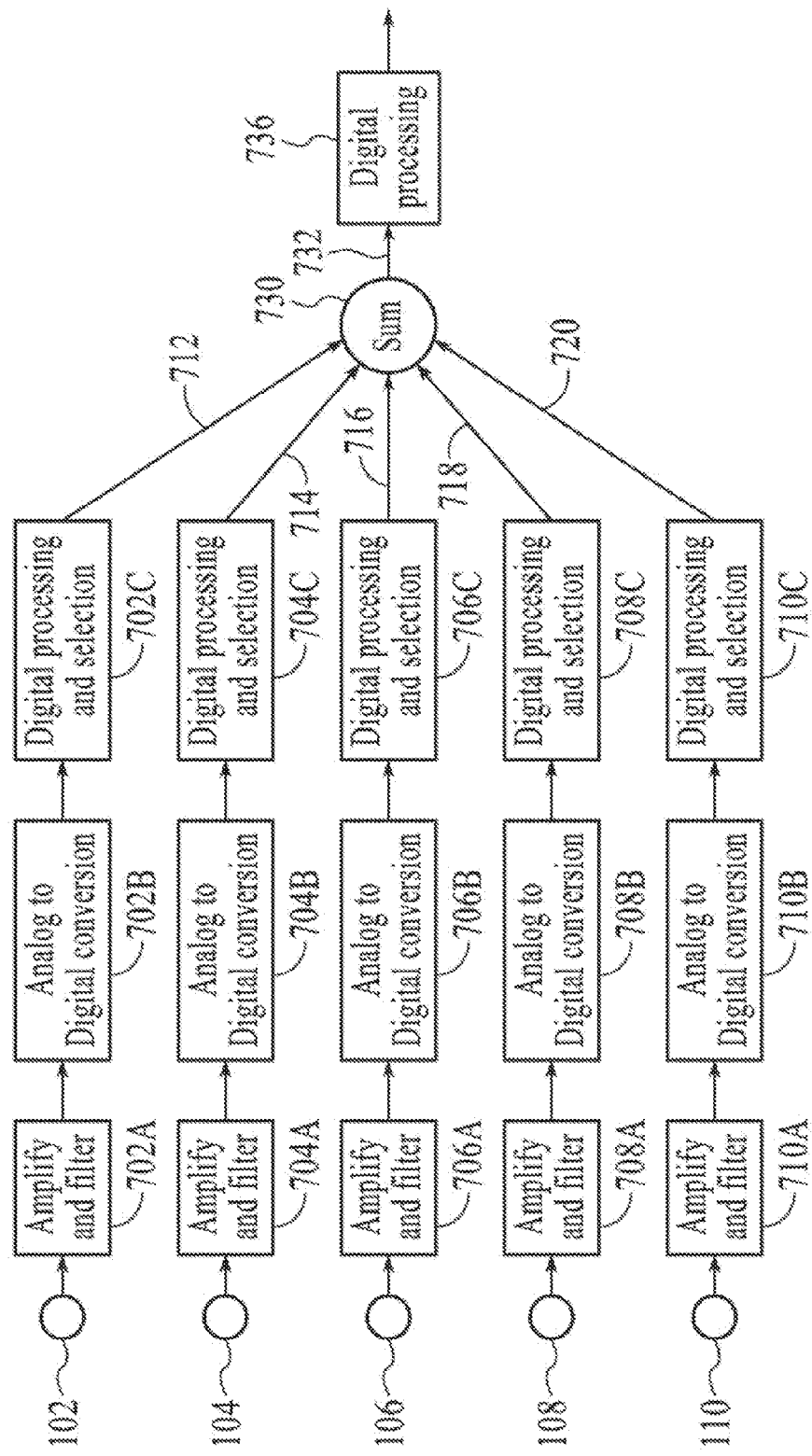

The signal processing of an embodiment includes methods for selecting high quality contact(s) and/or rejecting low quality contact(s) in an electrode based on signals collected by the electrodes. FIGS. 7A and 7B show a method for processing signals from a plurality of independent contacts 102-110 of an electrode in order to select high quality contact(s) and/or reject low quality contact(s) in an electrode based on signals collected by the electrodes, under an embodiment. In this embodiment, a signal of each contact 102-110 of the electrode is processed independently using a separate signal path 702-710. The independently processed signals 712-720 from each of the contacts 102-110 are then summed 730 to form a single signal 732, and further processing 736 is applied to the signal output 732 of the summing operation 730 (e.g., amplifying, filtering, signal conversion (e.g., analog to digital conversion), digital processing, etc.).

For example, amplifying and filtering 702A, analog to digital conversion 702B, and digital processing and selection 702C are applied to an output of a first contact 102 to form a first processed signal 712, amplifying and filtering 704A, analog to digital conversion 704B, and digital processing and selection 704C are applied to an output of a second contact 102 to form a second processed signal 714, amplifying and filtering 706A, analog to digital conversion 706B, and digital processing and selection 706C are applied to an output of a third contact 106 to form a third processed signal 716, amplifying and filtering 708A, analog to digital conversion 708B, and digital processing and selection 708C are applied to an output of a fourth contact 108 to form a fourth processed signal 718, and amplifying and filtering 710A, analog to digital conversion 710B, and digital processing and selection 710C are applied to an output of a fifth contact 110 to form a fifth processed signal 720. Following creation of the five processed signals 712-720, the five processed signals 712-720 are summed 730 to form a single signal 732, and further processing 736 is applied to the signal output 732 of the summing operation 730 (e.g., amplifying, filtering, signal conversion (e.g., analog to digital conversion), digital processing, etc.).

FIG. 7B shows an example method of digital processing to provide optimized signal output. For example, the example method includes an optimizing function shown as the residual of actual voltage, V(t), and the impulse response, S1($t$), plus the step response, S2($t$). The example method also includes a function to calculate optimum coefficients, k1($t$) and k2($t$). The example optimizing function combining these variable is shown in Equation (1):

$$V(t)-k1(t)*S1(t)-k2(t)*S2(t)=\text{Output}(t) \qquad \text{Equation (1)}$$

Figure 8:
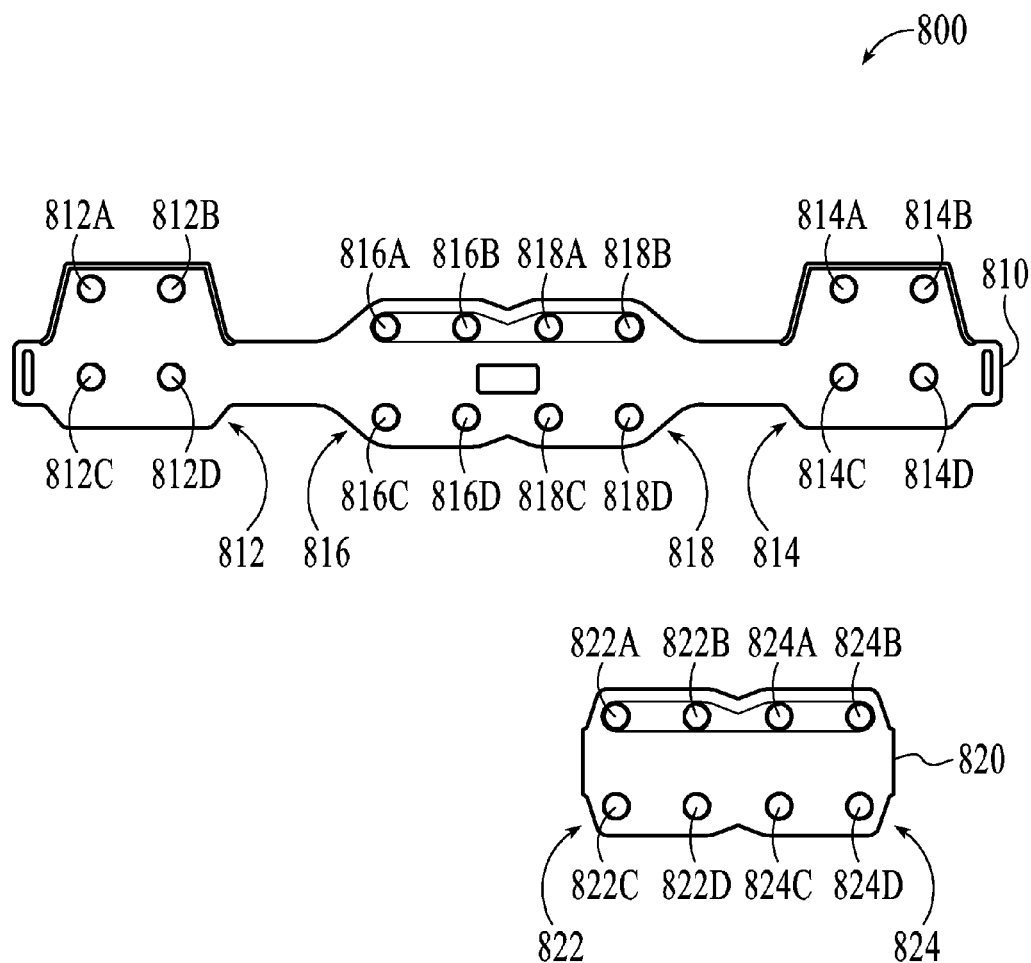
FIG. 8 shows an example of a sensor system, under an embodiment.

Multiple sensors or electrodes, each comprising a plurality of contacts as described above, can be combined to form a sensor system. FIG. 8 shows an example of a sensor system 800, under an embodiment. The sensor system 800 includes a first component 810 and a second component 820. The first component 810 comprises a left electrode 812 that includes four (4) contacts 812A-812D in close proximity to one another and arranged with each of the four contacts positioned in the corners of a rectangular configuration. The first component 810 also comprises a right electrode 814 that includes four (4) contacts 814A-814D in close proximity to one another and arranged with each of the four contacts positioned in the corners of a rectangular configuration.

Additionally, the first component 810 comprises two center electrodes 816-818 positioned adjacent to one another. A first center electrode 816 comprises four (4) contacts 816A-816D in close proximity to one another and arranged with each of the four contacts positioned in the corners of a rectangular configuration. A second center electrode 818 comprises four (4) contacts 818A-818D in close proximity to one another and arranged with each of the four contacts positioned in the corners of a rectangular configuration. The electrodes of the first component 810 are contained in a housing that is configured to be removeably attached to a subject.

The second component 820 comprises a left electrode 822 that includes four (4) contacts 822A-822D in close proximity to one another and arranged with each of the four contacts positioned in the corners of a rectangular configuration. The second component 820 also comprises a right electrode 824 that includes four (4) contacts 824A-824D in close proximity to one another and arranged with each of the four contacts positioned in the corners of a rectangular configuration. The electrodes of the second component 820 are contained in a housing that is configured to be removeably attached to a subject.

In an alternative embodiment, the electrodes of the first component and the second component are contained in a single housing. As yet another alternative, the electrodes of the first component and the second component can be contained in any number of housings.

Figure 9:
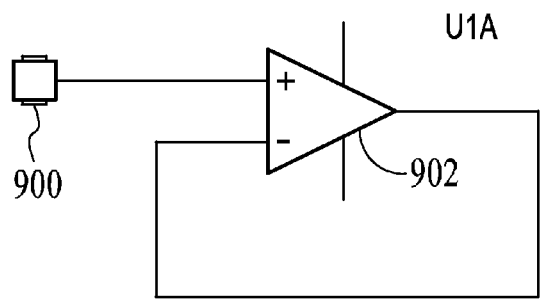
FIG. 9 shows circuit configurations of a contact coupled or connected to a single-ended amplifier, under an embodiment.
Figure 9:
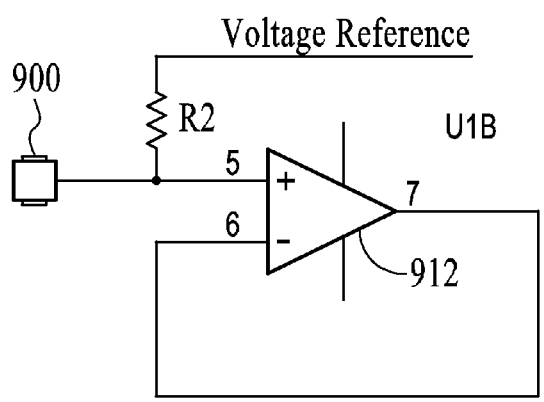

The contacts of an embodiment are coupled to a processor, as described above, via electronics or electronic circuits. FIG. 9 shows circuit configurations of a contact 900 coupled or connected to a single-ended amplifier 902/912, under an embodiment. The circuit configuration shown as element U1A includes a contact 900 coupled or connected to a single-ended amplifier 902, and this configuration works effectively in applications where the impedance of the contact and the ground reference are low enough (e.g., less than approximately $10^6$ ohms) to provide the small amount of bias current needed to keep the amplifiers in the linear reign.

An alternative configuration shown as element U1B includes a contact 900 coupled or connected to a single-ended amplifier 912 and a high impedance path (e.g., greater than approximately $10^8$ ohms) defined by resistor R2 and a voltage reference 904 that provides a small amount of bias current to keep the amplifier 912 in a linear region. This configuration allows the smooth gold contact to work as an electrode in applications that have higher impedance. While these examples couple or connect the contact to a single-ended amplifier, alternative embodiments couple or connect the contact to an instrumentation amplifier or any other high impedance amplification device.

In a wireless EEG measurement system the voltage of the system is not connected to an earth ground. Embodiments therefore include a method to control the voltage of the EEG measurement system to be balanced equally around the local voltage of the head. This is done by generating a voltage that is approximately halfway between the lowest voltage in the EEG measurement system and the highest voltage in the EEG measurement system. This voltage is then connected to a point that is in the area of the electronics or is at a similar voltage as the area of the electronics. This forces the voltage to float with respect to earth ground and to be similar to the local voltage of the measurement.

Figure 10:
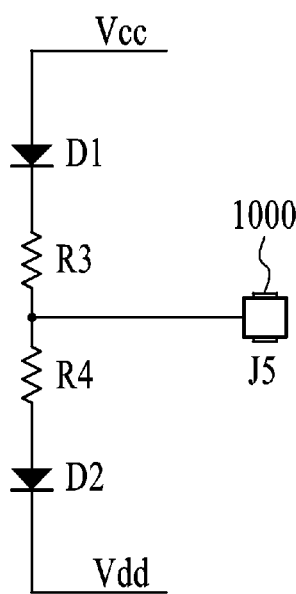
FIG. 10 shows a circuit that controls the voltage of the sensor system so as to be balanced equally around the local voltage of the head, under an embodiment.

FIG. 10 shows a circuit that controls the voltage of the sensor system so as to be balanced equally around the local voltage of the head, under an embodiment. This circuit includes an electrical path between Vcc and Vdd that comprises a diode D1 coupled between Vcc and resistor R3, a diode D2 coupled between Vdd and resistor R4, and contact 1000 coupled to resistors R3 and R4. This circuit generates a voltage that is approximately between the most positive voltage Vcc and most negative voltage Vdd in the floating system by using a diode or LED to drop some of the voltage and a pair of resistors to drop the remainder of the voltage, under an embodiment.

Figure 11:
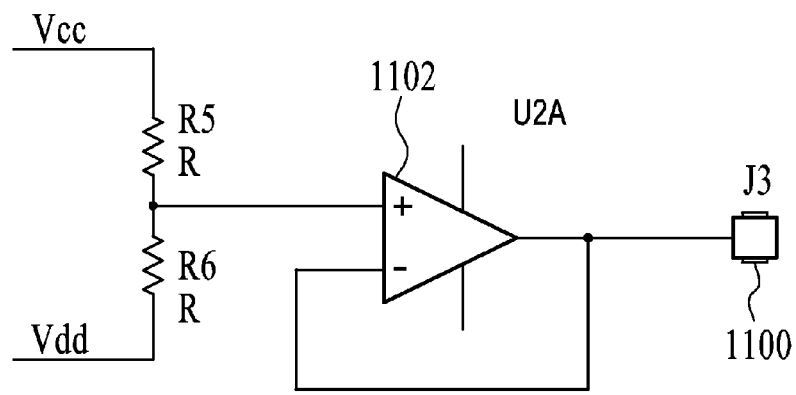
FIG. 11 shows a circuit that controls the voltage of the sensor system so as to be balanced equally around the local voltage of the head, under an alternative embodiment.

FIG. 11 shows a circuit that controls the voltage of the sensor system so as to be balanced equally around the local voltage of the head, under an alternative embodiment. This circuit includes two resistors R5 and R6 coupled in series between Vcc and Vdd, and an input of an operational amplifier 1102 coupled to resistors R5 and R6. A contact 1100 is coupled to an output of the operational amplifier 1102. This circuit uses two resistors and an operational amplifier to generate a voltage that is approximately between the most positive and negative voltages in the floating system, under an embodiment. In FIG. 10 and FIG. 11 the voltages Vcc and Vdd are the highest and lowest voltages in the system. This voltage can be used to keep the EEG measurement system in the appropriate voltage range and/or it can be used as a reference voltage for measurements.

Figure 12:
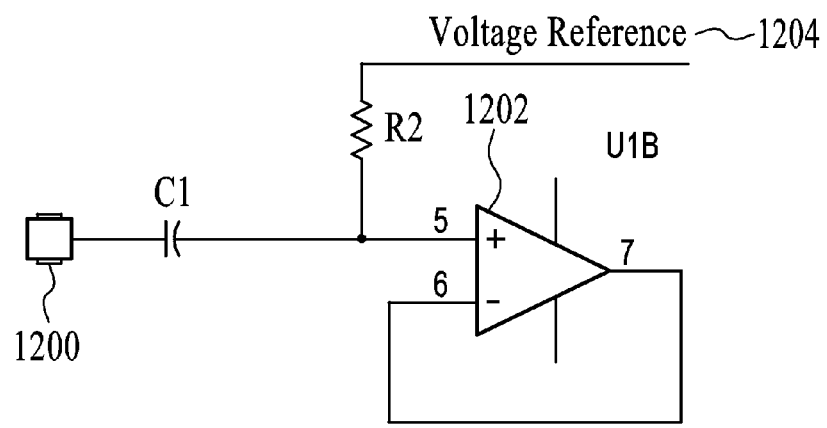
FIG. 12 is a circuit that eliminates any direct current (DC) path for the connection between the skin and the amplifier input, under an embodiment.

The contact of an embodiment makes contact with the skin through a resistive connection, or through a capacitive connection, or some combination of a resistive and capacitive connection. The combination of capacitive and resistive contact makes the algorithms to process the data difficult and adds uncertainty to the output. FIG. 12 is a circuit that eliminates any direct current (DC) path for the connection between the skin and the amplifier input, under an embodiment. This circuit includes a capacitor C1 coupled between a contact 1200 and an operational amplifier 1202. A high impedance path (e.g., greater than approximately $10^8$ ohms) defined by resistor R2 and a voltage reference 1204 provides a small amount of bias current to keep the amplifier 1202 in a linear region.

Mobile EEGs have a wireless link that transmits data from the sensor to a base station through a wireless or infrared link. Embodiments described herein include a mobile measurement system that comprises onboard memory and records the data from the sensor into memory that is downloaded and processed later. One embodiment includes a removable memory card (e.g., an SD card) that is inserted into a slot in the sensor. At the end of a test the card is removed and the data read into a computer. An alternative embodiment includes memory built into the sensor system, and the data is stored in the memory of the system during a test and downloaded through a link after the test. This link can be USB, RS232, wireless, or any other available link.

The second component comprises a rear element that includes two center electrodes positioned adjacent to one another, and each center electrode includes four (4) contacts in close proximity to one another and arranged with each of the four contacts positioned in the corners of a rectangular configuration. The electrodes of the second component are also contained in a housing that is configured to be removeably attached to a subject. The first and second components are shown as contained in separate housings, but the embodiment is not so limited. For example, an alternative embodiment can house the first and second components in a single housing. In another alternative embodiment, the electrodes of the first and second components can be combined in numerous other configurations and contained in any number of housings.

The sensor system of an embodiment includes one or more processors carried onboard the system. The processor(s) is coupled to the contacts that form the sensors, and processes the signals from the contacts. The processing includes, but is not limited to, amplifying, filtering, signal conversion, signal combining, combining multiple data streams into one time-synchronized format, and processing signals for wireless transmission. The sensor system measures and processes physiological data, for example, EEG, heart rate, blink, blink rate, respiration rate, physical movement, muscle movement, eye movement, and temperature data to name a few.

Embodiments described herein include an apparatus comprising a plurality of sensor electrodes. Each sensor electrode comprises a plurality of contacts positioned adjacent one another to form a pattern. The apparatus of an embodiment includes a plurality of signal outputs coupled to the plurality of contacts. A signal output of the plurality of signal outputs is connected to each contact of the plurality of contacts. The apparatus of an embodiment includes at least one processor coupled to the plurality of signal outputs. The processor separately processes each signal output of the plurality of signal outputs.

Embodiments described herein include an apparatus comprising: a plurality of sensor electrodes, wherein each sensor electrode comprises a plurality of contacts positioned adjacent one another to form a pattern; a plurality of signal outputs coupled to the plurality of contacts, wherein a signal output of the plurality of signal outputs is connected to each contact of the plurality of contacts; and at least one processor coupled to the plurality of signal outputs, wherein the processor separately processes each signal output of the plurality of signal outputs.

The apparatus of an embodiment comprises a first housing that includes a first plurality of sensor electrodes, and a second housing that includes a second plurality of sensor electrodes.

The first housing of an embodiment comprises a left sensor electrode on a first end of the first housing, and a right sensor electrode on a second end of the first housing.

The apparatus of an embodiment comprises a left center sensor electrode positioned in the first housing between the first end and a center region of the first housing, and a right center sensor electrode positioned in the first housing between the second end and the center region.

The left sensor electrode of an embodiment is configured to contact a left region of a human head, the right sensor electrode is configured to contact a right region of the human head, and the left center sensor electrode and the right center sensor electrode are configured to contact a front center region of the human head when worn by a subject.

The plurality of contacts of each sensor electrode of the first plurality of sensor electrodes of an embodiment comprises four contacts and the pattern comprises a rectangle, wherein a contact is positioned in each corner region of the rectangle.

The second housing of an embodiment comprises a left rear sensor electrode on a first end of the second housing, and a right rear sensor electrode on a second end of the second housing.

The left rear sensor electrode and the right rear sensor electrode of an embodiment are configured to contact a rear center region of the human head when worn by the subject.

The plurality of contacts of each sensor electrode of the second plurality of sensor electrodes of an embodiment comprises four contacts and the pattern comprises a rectangle, wherein a contact is positioned in each corner region of the rectangle.

The apparatus of an embodiment comprises a substrate connected to the first housing and the second housing.

The plurality of contacts of each sensor electrode of an embodiment comprises four contacts and the pattern comprises a rectangle, wherein a contact is positioned in each corner region of the rectangle.

The plurality of contacts of each sensor electrode of an embodiment comprises five contacts and the pattern comprises a rectangle, wherein a contact is positioned in each corner region of the rectangle, and a contact is positioned in a center region of the rectangle.

A distance between a first contact in a first corner and a second contact in a second corner of an embodiment is approximately 1.25 inches.

The processor of an embodiment separately processes the signal outputs of each of the plurality of contacts.

The processor of an embodiment forms a plurality of processed signals by separately processing the signal outputs of each of the plurality of contacts, and forms a combined signal by combining the plurality of processed signals.

The plurality of contacts of an embodiment comprises gold contacts.

The apparatus of an embodiment comprises an input of single-ended amplifier coupled to a signal output of at least one contact of the plurality of contacts.

The apparatus of an embodiment comprises a biasing circuit coupled to the input of the single-ended amplifier, wherein the biasing circuit comprises a resistor coupled between a voltage source and the input of the single-ended amplifier.

The apparatus of an embodiment comprises a voltage balancing circuit coupled to a signal output of at least one contact of the plurality of contacts.

The voltage balancing circuit of an embodiment comprises a first resistor and a second resistor coupled in series and coupled to the signal output of the at least one contact, wherein a first diode couples the first resistor to a first voltage source, wherein a second diode couples the second resistor to a second voltage source.

The voltage balancing circuit of an embodiment comprises an output of a single-ended amplifier coupled to the signal output of the at least one contact, and a first resistor and a second resistor coupled in series between a first voltage source and a second voltage source and coupled to an input of the single-ended amplifier.

The apparatus of an embodiment comprises a direct current elimination circuit coupled to at least one contact of the plurality of contacts.

The direct current elimination circuit of an embodiment comprises a capacitor coupled between an input of a single-ended amplifier and a signal output of the at least one contact.

The direct current elimination circuit of an embodiment comprises a biasing circuit coupled to the contact and the single-ended amplifier, wherein the biasing circuit comprises a resistor coupled between a voltage source and the input of the single-ended amplifier.

The apparatus of an embodiment comprises a wireless transmitter coupled to the processor, wherein the wireless transmitter transmits data of the plurality of contacts.

Embodiments described herein include a system comprising at least one housing that is removeably attachable to a subject. The system of an embodiment includes a plurality of sensor electrodes. Each sensor electrode comprises a plurality of contacts positioned adjacent one another to form a pattern. The system of an embodiment includes a plurality of signal outputs coupled to the plurality of contacts. A signal output of the plurality of signal outputs is connected to each contact of the plurality of contacts. The system of an embodiment includes at least one control circuit positioned in the at least one housing and coupled to the plurality of signal outputs. The system of an embodiment includes at least one processor positioned in the housing and coupled to the at least one control circuit. The processor separately processes each signal output of the plurality of signal outputs.

Embodiments described herein include a system comprising: at least one housing that is removeably attachable to a subject; a plurality of sensor electrodes, wherein each sensor electrode comprises a plurality of contacts positioned adjacent one another to form a pattern; a plurality of signal outputs coupled to the plurality of contacts, wherein a signal output of the plurality of signal outputs is connected to each contact of the plurality of contacts; and at least one control circuit positioned in the at least one housing and coupled to the plurality of signal outputs; and at least one processor positioned in the housing and coupled to the at least one control circuit, wherein the processor separately processes each signal output of the plurality of signal outputs.

The at least one housing of an embodiment comprises a first housing that includes a first plurality of sensor electrodes, and a second housing that includes a second plurality of sensor electrodes.

The first housing of an embodiment comprises a left sensor electrode on a first end of the first housing, and a right sensor electrode on a second end of the first housing.

The system of an embodiment comprises a left center sensor electrode positioned in the first housing between the first end and a center region of the first housing, and a right center sensor electrode positioned in the first housing between the second end and the center region.

The left sensor electrode of an embodiment is configured to contact a left region of a human head, the right sensor electrode is configured to contact a right region of the human head, and the left center sensor electrode and the right center sensor electrode are configured to contact a front center region of the human head when worn by a subject.

The plurality of contacts of each sensor electrode of the first plurality of sensor electrodes of an embodiment comprises four contacts and the pattern comprises a rectangle, wherein a contact is positioned in each corner region of the rectangle.

The second housing of an embodiment comprises a left rear sensor electrode on a first end of the second housing, and a right rear sensor electrode on a second end of the second housing.

The left rear sensor electrode and the right rear sensor electrode of an embodiment are configured to contact a rear center region of the human head when worn by the subject.

The plurality of contacts of each sensor electrode of the second plurality of sensor electrodes of an embodiment comprises four contacts and the pattern comprises a rectangle, wherein a contact is positioned in each corner region of the rectangle.

The system of an embodiment comprises a substrate connected to the first housing and the second housing.

The plurality of contacts of each sensor electrode of an embodiment comprises four contacts and the pattern comprises a rectangle, wherein a contact is positioned in each corner region of the rectangle.

The plurality of contacts of each sensor electrode of an embodiment comprises five contacts and the pattern comprises a rectangle, wherein a contact is positioned in each corner region of the rectangle, and a contact is positioned in a center region of the rectangle.

A distance between a first contact in a first corner and a second contact in a second corner of an embodiment is approximately 1.25 inches.

The processor of an embodiment separately processes the signal outputs of each of the plurality of contacts.

The processor of an embodiment forms a plurality of processed signals by separately processing the signal outputs of each of the plurality of contacts, and forms a combined signal by combining the plurality of processed signals.

The plurality of contacts of an embodiment comprises gold contacts.

The at least one control circuit of an embodiment comprises a single-ended amplifier having an input coupled to a signal output of at least one contact of the plurality of contacts.

The at least one control circuit of an embodiment comprises a biasing circuit coupled to the input of the single-ended amplifier, wherein the biasing circuit comprises a resistor coupled between a voltage source and the input of the single-ended amplifier.

The at least one control circuit of an embodiment comprises a voltage balancing circuit coupled to a signal output of at least one contact of the plurality of contacts.

The voltage balancing circuit of an embodiment comprises a first resistor and a second resistor coupled in series and coupled to the signal output of the at least one contact, wherein a first diode couples the first resistor to a first voltage source, wherein a second diode couples the second resistor to a second voltage source.

The voltage balancing circuit of an embodiment comprises an output of a single-ended amplifier coupled to the signal output of the at least one contact, and a first resistor and a second resistor coupled in series between a first voltage source and a second voltage source and coupled to an input of the single-ended amplifier.

The at least one control circuit of an embodiment comprises a direct current elimination circuit coupled to at least one contact of the plurality of contacts.

The direct current elimination circuit of an embodiment comprises a capacitor coupled between an input of a single-ended amplifier and a signal output of the at least one contact.

The direct current elimination circuit of an embodiment comprises a biasing circuit coupled to the contact and the single-ended amplifier, wherein the biasing circuit comprises a resistor coupled between a voltage source and the input of the single-ended amplifier.

The system of an embodiment comprises a wireless transmitter coupled to the processor, wherein the wireless transmitter transmits data of the plurality of contacts.

The electrodes can be components of a single system, multiple systems, and/or geographically separate systems. The electrodes can also be subcomponents or subsystems of a single system, multiple systems, and/or geographically separate systems. The electrodes can be coupled to one or more other components (not shown) of a host system or a system coupled to the host system.

The electrodes of an embodiment include and/or run under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, cellular telephones, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components of the AMS, and/or provided by some combination of algorithms. The AMS methods described herein can be implemented in one or more of software algorithm(s), programs, firmware, hardware, components, circuitry, in any combination.

Components of the processing system used with the electrodes of an embodiment can be located together or in separate locations. Communication paths couple the electrodes and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the electrodes and corresponding systems described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the electrodes and corresponding systems include: microcontrollers with memory (such as electronically erasable programmable read only memory (EEPROM)), embedded microprocessors, firmware, software, etc. Furthermore, aspects of the electrodes and corresponding systems may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the electrodes is not intended to be exhaustive or to limit the systems and methods to the precise forms disclosed. While specific embodiments of, and examples for, the electrodes are described herein for illustrative purposes, various equivalent modifications are possible within the scope of the systems and methods, as those skilled in the relevant art will recognize. The teachings of the electrodes provided herein can be applied to other systems and methods, not only for the systems and methods described above.

The elements and acts of the various embodiments described above can be combined to provide further embodiments. These and other changes can be made to the electrodes in light of the above detailed description.

What is claimed is:

1. An apparatus comprising:
a plurality of sensor electrodes, each sensor electrode comprising a plurality of contacts;
a plurality of signal outputs coupled to the plurality of contacts;

a processor coupled to the plurality of signal outputs, the processor to separately process each signal output of the plurality of signal outputs; and a voltage balancing circuit coupled to a signal output of at least one contact of the plurality of contacts, wherein the voltage balancing circuit comprises an output of a single-ended amplifier coupled to the signal output of the at least one contact, and a first resistor and a second resistor coupled in series between a first voltage source and a second voltage source and coupled to an input of the single-ended amplifier.

2. The apparatus of claim 1, wherein the plurality of sensor electrodes comprises:

a first electrode to be coupled to a first portion of a body of a human subject, the first electrode comprising:
 a first contact to gather a first signal from the first portion of the body; and
 a second contact to gather a second signal from the first portion of the body;

a second electrode to be coupled to a second portion of the body, the second electrode comprising:
 a third contact to gather a third signal from the second portion of the body; and
 a fourth contact to gather a fourth signal from the second portion of the body; and wherein the processor is communicatively coupled to the first electrode and the second electrode to separately process the first signal, the second signal, the third signal and the fourth signal.

3. The apparatus of claim 2 further comprising:
a first housing that includes the first electrode and a third electrode; and
a second housing that includes the second electrode and a fourth electrode.

4. The apparatus of claim 3, wherein the first electrode is disposed on a first end of the first housing, and the third electrode is disposed on a second end of the first housing.

5. The apparatus of claim 4 further comprising:
a fifth electrode positioned in the first housing between the first end and a center region of the first housing; and
a sixth electrode positioned in the first housing between the second end and the center region.

6. The apparatus of claim 5, wherein the first electrode is to contact a left region of a head of the body, the third electrode is to contact a right region of the head, and the fifth electrode and the sixth electrode are to contact a front center region of the head when worn by the subject.

7. The apparatus of claim 3, wherein the first electrode further comprises a fifth contact and a sixth contact, the first contact, the second contact, the fifth contact and the sixth contact being arranged in a rectangular pattern with each of the first contact, the second contact, the fifth contact and the sixth contact positioned in a respective corner region of the rectangular pattern.

8. The apparatus of claim 7, wherein the second electrode further comprises a seventh contact and an eighth contact, the third contact, the fourth contact, the seventh contact and the eighth contact being arranged in a rectangular pattern with each of the third contact, the fourth contact, the seventh contact and the eighth contact positioned in a respective corner region of the rectangular pattern.

9. The apparatus of claim 1, wherein the second electrode is disposed on a first end of the second housing, and the fourth electrode on a second end of the second housing.

10. The apparatus of claim 9, wherein the second electrode and the fourth electrode are to contact a rear center region of a head of the body when worn by the subject.

11. The apparatus of claim 9, comprising a substrate connected to the first housing and the second housing.

12. The apparatus of claim 2, wherein the first electrode further comprises a fifth contact and a sixth contact, the first contact, the second contact, the fifth contact and the sixth contact being arranged in a rectangular pattern with each of the first contact, the second contact, the fifth contact and the sixth contact positioned in a respective corner region of the rectangular pattern.

13. The apparatus of claim 2, wherein the first electrode further comprises a fifth contact, a sixth contact and a seventh contact, the first contact, the second contact, the fifth contact, the sixth contact and the seventh contact being arranged in a rectangular pattern with each of the first contact, the second contact, the fifth contact, and the sixth contact positioned in a respective corner region of the rectangular pattern, and the seventh contact positioned in a center region of the rectangular pattern.

14. The apparatus of claim 13, wherein a distance between the first contact in a first corner and the second contact in a second corner is approximately 1.25 inches.

15. The apparatus of claim 2, wherein the processor is to form a plurality of processed signals by separately processing the first signal, the second signal, the third signal and the fourth signal, and the processor is to form a combined signal by combining at least two of the first signal, the second signal, the third signal and the fourth signal when processed.

16. The apparatus of claim 2, wherein at least one of the first contact, the second contact, the third contact or the fourth contact comprises gold.

17. The apparatus of claim 2 further comprising a wireless transmitter communicatively coupled to the processor, the wireless transmitter to transmit one or more of: (1) data of at least one of the first contact, the second contact, the third contact or the fourth contact or (2) data gathered by at least one of the first contact, the second contact, the third contact or the fourth contact.

18. The apparatus of claim 1, wherein the single-ended amplifier is a first single-ended amplifier and the input is a first input, the apparatus further comprising a second input of a second single-ended amplifier communicatively coupled to at least one of the plurality of contacts.

19. The apparatus of claim 18, further comprising a biasing circuit in circuit with the second single-ended amplifier, wherein the biasing circuit comprises a third resistor coupled between a third voltage source and the second single-ended amplifier.

20. The apparatus of claim 1, wherein the voltage balancing circuit is a first voltage balancing circuit, the apparatus further comprising a second voltage balancing circuit communicatively coupled to a second one of the plurality of contacts.

21. The apparatus of claim 20, wherein the second voltage balancing circuit comprises a third resistor and a fourth resistor in circuit with the second one of the plurality of contacts, wherein a first diode couples the third resistor to a third voltage source, and a second diode couples the fourth resistor to a fourth voltage source.

22. The apparatus of claim 1 further comprising a direct current elimination circuit communicatively coupled to at least one of the plurality of contacts.

23. The apparatus of claim 22, wherein the single-ended amplifier is a first single-ended amplifier and the input is a first input, and wherein the direct current elimination circuit comprises a capacitor coupled between a second input of a second single-ended amplifier and the at least one of the plurality of contacts communicatively coupled to the direct current elimination circuit.

24. The apparatus of claim 23, wherein the direct current elimination circuit comprises a biasing circuit communicatively coupled to the at least one of the plurality of contacts communicatively coupled to the direct current elimination circuit, and wherein the biasing circuit comprises a third resistor coupled between a third voltage source and the second input of the second single-ended amplifier.

25. A system comprising:
a plurality of sensor electrodes, each sensor electrode comprising a plurality of contacts;
a plurality of signal outputs coupled to the plurality of contacts;
a control circuit coupled to the plurality of signal outputs; and
a processor coupled to the control circuit, the processor to separately process each signal output of the plurality of signal outputs,
wherein the control circuit comprises a voltage balancing circuit coupled to a signal output of at least one contact of the plurality of contacts, and
wherein the voltage balancing circuit comprises an output of a single-ended amplifier coupled to the signal output of the at least one contact, and a first resistor and a second resistor coupled in series between a first voltage source and a second voltage source and coupled to an input of the single-ended amplifier.

26. The system of claim 25, wherein the plurality of sensor electrodes comprises:
a first electrode to be coupled to a first portion of a body of a human subject, the first electrode comprising:
a first contact to gather a first signal from the first portion of the body; and
a second contact to gather a second signal from the first portion of the body;
a second electrode to be coupled to a second portion of the body, the second electrode comprising:
a third contact to gather a third signal from the second portion of the body; and
a fourth contact to gather a fourth signal from the second portion of the body;
wherein the control circuit is communicatively coupled to the first contact, the second contact, the third contact and the fourth contact; and
wherein the processor is to separately process the first signal, the second signal, the third signal and the fourth signal.

27. The system of claim 26 further comprising:
a first housing that includes the first electrode and a third electrode; and
a second housing that includes the second electrode and a fourth electrode.

28. The system of claim 27, wherein the first electrode is disposed on a first end of the first housing, and the third electrode is disposed on a second end of the first housing.

29. The system of claim 28 further comprising:
a fifth electrode positioned in the first housing between the first end and a center region of the first housing; and
a sixth electrode positioned in the first housing between the second end and the center region.

30. The system of claim 29, wherein the first electrode is to contact a left region of a head of the body, the third electrode is to contact a right region of the head, and the fifth electrode and the sixth electrode are to contact a front center region of the head when worn by the subject.

31. The system of claim 27, wherein the first electrode further comprises a fifth contact and a sixth contact, the first contact, the second contact, the fifth contact and the sixth contact being arranged in a rectangular pattern with each of the first contact, the second contact, the fifth contact and the sixth contact positioned in a respective corner region of the rectangular pattern.

32. The system of claim 27, wherein the second electrode is disposed on a first end of the second housing, and the fourth electrode on a second end of the second housing.

33. The system of claim 32, wherein the second electrode and the fourth electrode are to contact a rear center region of a head of the body when worn by the subject.

34. The system of claim 32, wherein the second electrode further comprises a seventh contact and an eighth contact, the third contact, the fourth contact, the seventh contact and the eighth contact being arranged in a rectangular pattern with each of the third contact, the fourth contact, the seventh contact and the eighth contact positioned in a respective corner region of the rectangular pattern.

35. The system of claim 32, comprising a substrate connected to the first housing and the second housing.

36. The system of claim 26, wherein the first electrode further comprises a fifth contact and a sixth contact, the first contact, the second contact, the fifth contact and the sixth contact being arranged in a rectangular pattern with each of the first contact, the second contact, the fifth contact and the sixth contact positioned in a respective corner region of the rectangular pattern.

37. The system of claim 26, wherein the first electrode further comprises a fifth contact, a sixth contact and a seventh contact, the first contact, the second contact, the fifth contact, the sixth contact and the seventh contact being arranged in a rectangular pattern with each of the first contact, the second contact, the fifth contact and the sixth contact positioned in a respective corner region of the rectangular pattern, and the seventh contact positioned in a center region of the rectangular pattern.

38. The system of claim 37, wherein a distance between the first contact in a first corner and the second contact in a second corner is approximately 1.25 inches.

39. The system of claim 26, wherein the processor is to form a plurality of processed signals by separately processing the first signal, the second signal, the third signal and the fourth signal, and the processor is to form a combined signal by combining at least two of the first signal, the second signal, the third signal and the fourth signal when processed.

40. The system of claim 26, wherein at least one of the first contact, the second contact, the third contact or the fourth contact comprises gold.

41. The system of claim 26 further comprising a wireless transmitter communicatively coupled to the processor, the wireless transmitter to transmit one or more of: (1) data of at least one of the first contact, the second contact, the third contact or the fourth contact or (2) data gathered by at least one of the first contact, the second contact, the third contact or the fourth contact.

42. The system of claim 25, wherein the single-ended amplifier is a first single-ended amplifier and the input is a first input, and wherein the control circuit comprises a second single-ended amplifier having a second input communicatively coupled to at least one of the plurality of contacts.

43. The system of claim 42, wherein the control circuit comprises a biasing circuit in circuit with the second single-ended amplifier, wherein the biasing circuit comprises a third resistor coupled between a third voltage source and the second single-ended amplifier.

44. The system of claim 25, wherein the voltage balancing circuit is a first voltage balancing circuit, and wherein the control circuit comprises a second voltage balancing circuit communicatively coupled to a second one of the plurality of contacts.

45. The system of claim 44, wherein the second voltage balancing circuit comprises a third resistor and a fourth resistor in circuit with the second one of the plurality of contacts, a first diode couples the third resistor to a third voltage source, and a second diode couples the fourth resistor to a fourth voltage source.

46. The system of claim 25, wherein the control circuit comprises a direct current elimination circuit communicatively coupled to at least one of the plurality of contacts.

47. The system of claim 46, wherein the single-ended amplifier is a first single-ended amplifier and the input is a first input, and wherein the direct current elimination circuit comprises a capacitor in circuit with a second input of a second single-ended amplifier and the at least one of the plurality of contacts communicatively coupled to the direct current elimination circuit.

48. The system of claim 47, wherein the direct current elimination circuit comprises a biasing circuit communicatively coupled to the at least one of the plurality of contacts communicatively coupled to the direct current elimination circuit, and the biasing circuit comprises a third resistor coupled between a third voltage source and the input of the second single-ended amplifier.

* * * * *